United States Patent
Palmer (10) Patent No.: US 11,760,710 B2
(45) Date of Patent: Sep. 19, 2023

(54) TREATMENT OF RESIDUAL STREAMS FROM THE MANUFACTURE OF BISPHENOLS

(71) Applicant: BADGER LICENSING LLC, Boston, MA (US)

(72) Inventor: David Palmer, Katy, TX (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 17/257,356

(22) PCT Filed: Jul. 6, 2018

(86) PCT No.: PCT/US2018/041024
§ 371 (c)(1),
(2) Date: Dec. 31, 2020

(87) PCT Pub. No.: WO2020/009705
PCT Pub. Date: Jan. 9, 2020

(65) Prior Publication Data
US 2021/0363082 A1    Nov. 25, 2021

(51) Int. Cl.
C07C 37/86    (2006.01)
C07C 37/20    (2006.01)
C07C 37/84    (2006.01)

(52) U.S. Cl.
CPC .............. C07C 37/86 (2013.01); C07C 37/20 (2013.01); C07C 37/84 (2013.01)

(58) Field of Classification Search
CPC .......... C07C 37/86; C07C 37/20; C07C 37/84
See application file for complete search history.

(56) References Cited

U.S. PATENT DOCUMENTS

| | | | | |
|---|---|---|---|---|
| 4,107,218 A | * | 8/1978 | Konrad | C07C 39/16 |
| | | | | 568/724 |
| 5,315,042 A | * | 5/1994 | Cipullo | C07C 37/20 |
| | | | | 528/129 |
| 5,336,812 A | | 8/1994 | Salek et al. | |
| 6,133,486 A | * | 10/2000 | Maas | C07C 37/50 |
| | | | | 568/728 |
| 6,653,513 B1 | | 11/2003 | Iwahara | |
| 7,820,866 B2 | | 10/2010 | Fetsko et al. | |
| 7,858,830 B2 | | 12/2010 | Evitt et al. | |
| 2005/0215833 A1 | | 9/2005 | Neumann et al. | |
| 2005/0222467 A1 | | 10/2005 | Kodama et al. | |
| 2010/0105960 A1 | | 4/2010 | Evitt et al. | |
| 2012/0010434 A1 | | 1/2012 | Tsutsuminai et al. | |
| 2012/0310014 A1 | | 12/2012 | Palmer et al. | |
| 2012/0310015 A1 | | 12/2012 | Palmer et al. | |
| 2013/0221837 A1 | | 8/2013 | De Brouwer et al. | |
| 2014/0121417 A1 | | 5/2014 | Youssef et al. | |

FOREIGN PATENT DOCUMENTS

WO    2007/130040 A1    11/2007
WO    2007132575 A1    11/2007

OTHER PUBLICATIONS

International Search report and Written Opinion issued in the corresponding Application No. PCT/US2018/041024 dated Mar. 28, 2019.

* cited by examiner

*Primary Examiner* — Rosalynd A Keys
(74) *Attorney, Agent, or Firm* — Peter W. Roberts; Calderon Safran & Cole P.C.

(57) ABSTRACT

A method is disclosed for treating a residual stream from bisphenol manufacture, wherein the residual stream comprises unreacted phenols, bisphenol isomers, trisphenols, organic sulfides and water. The method comprises contacting at least a portion of the residual stream or a reaction product thereof with an acidic catalyst under conditions sufficient to allow acid-catalyzed hydrolysis of organic sulfides in the residual stream to the corresponding thiols and produce an effluent stream, and then distilling at least a portion of the effluent stream to recover distillate products comprising phenols and thiols and produce a bottoms product comprising bisphenol isomers and trisphenols, and having a lower content of organic sulfides than the residual stream.

22 Claims, 5 Drawing Sheets

TREATMENT OF RESIDUAL STREAMS FROM THE MANUFACTURE OF BISPHENOLS

CROSS-REFERENCE TO RELATED APPLICATIONS

The present application is a U.S. National Phase of PCT/US2018/041024 filed on Jul. 6, 2018. The disclosure of the PCT Application is hereby incorporated by reference into the present Application.

FIELD

This invention relates to treatment of residual streams from the manufacture of bisphenols, particularly the manufacture of bisphenol-A, for the purpose of removing and recovering sulfur compounds.

BACKGROUND

Bisphenol-A (BPA), also referred to as 2,2-bis (4-hydroxyphenyl) propane or para, para-diphenylolpropane (p,p-BPA), is a commercially significant compound used to manufacture polycarbonates, other engineering thermoplastics and epoxy resins. The polycarbonate application in particular demands high purity BPA due to stringent requirements for optical clarity and color in the finished application. BPA is produced commercially by the condensation of acetone and phenol and, in fact, BPA production is the largest consumer of phenol. The condensation reaction may take place in the presence of a strong homogenous acid, such as hydrochloric acid, sulfuric acid, or toluene sulfonic acid, or in the presence of a heterogeneous acid catalyst, such as a sulfonated ion exchange resin. In recent years, acidic ion exchange resins have become the overwhelming choice as catalysts for the condensation reaction of bisphenol manufacture, and strongly acidic sulfonated polystyrene ion exchange resins are particularly useful in this regard.

Two different techniques for employing heterogeneous acid catalysts in bisphenols production predominate in industrial practice. In one technique, a cocatalyst is freely circulated in the reactor with the reaction feed. It is used to enhance the selectivity and/or activity of the reaction. An alkanethiol, such as methyl or ethyl mercaptan, or a mercaptocarboxylic acid, such as 3-mercaptopropionic acid, is typically used as the freely circulating cocatalyst in this technique.

In the second technique for employing heterogeneous acid catalysts in the production of bisphenols, the catalyst is modified by appending cocatalytic agents, such as thiazolidines and aminothiols, to some of the acid sites on the catalyst. For example, mercapto-promoter groups may be attached to backbone sulfonate ions of a cation exchange resin by covalent or ionic nitrogen linkages.

One problem associated with the use of sulfur-containing promoters in the manufacture of bisphenols is that thiols, particularly methyl mercaptans, also react with carbonyls and other unsaturated intermediates to form sulfides. These heavier sulfides are present in the reactor product and also in the residual stream remaining after recovery of the desired bisphenol product. Presently, at least part of the residual stream is subsequently distilled to recover a phenol and water distillate, leaving the heavy sulfides in the bottoms stream from the distillation process. This not only increases consumption of the thiol promoter but also contaminates the bottoms stream which makes disposal and/or further processing of this bottoms stream more complex.

Accordingly, in the manufacture of bisphenols using sulfur-containing promoters, a way is needed to remove the sulfide contaminants from the residual streams remaining after recovery of the desired bisphenol product and to recover the thiol promoter from the sulfide contaminants.

SUMMARY

In one aspect, the present invention relates to a method for treating a residual stream from bisphenol manufacture, wherein the residual stream comprises unreacted phenols, bisphenol isomers, trisphenols, organic sulfides and water and wherein the method comprises:

(a1) contacting at least a portion of the residual stream or a reaction product thereof with an acidic catalyst under conditions sufficient to allow acid-catalyzed hydrolysis of organic sulfides in the residual stream to the corresponding thiols and produce an effluent stream; and (b1) distilling at least a portion of the effluent stream to recover distillate products comprising phenols and thiols and produce a bottoms product comprising bisphenol isomers and trisphenols, and having a lower content of organic sulfides than the residual stream.

In a further aspect, the present invention relates to a method for producing bisphenol-A comprising:

(a2) condensing acetone with a molar excess of phenol in the presence of a first solid acid catalyst promoted with a thiol under conditions effective to produce a first effluent stream comprising bisphenol isomers, unreacted phenol, trisphenols, organic sulfides and water;

(b2) recovering bisphenol-A from the first effluent stream to leave a residual stream comprising a mixture of bisphenol isomers depleted in bisphenol-A, unreacted phenol, trisphenols, organic sulfides and water;

(c2) contacting at least part of the residual stream with a second catalyst under conditions effective to isomerize bisphenol isomers to bisphenol-A and to hydrolyze organic sulfides to the corresponding thiols and produce a second effluent stream;

(d2) dividing the second effluent stream into a recycle stream and a purge stream;

(e2) supplying the recycle stream to step (a2) or step (b2);

(f2) distilling the purge stream or a reaction product thereof to recover distillate products comprising phenol and thiols and produce a bottoms product comprising bisphenol isomers and trisphenols and having a lower content of organic sulfides than the residual stream; and (g2) supplying the distillate products recovered in step (f2) to step (a2).

In yet a further aspect, the present invention relates to a method for producing bisphenol-A comprising:

(a3) condensing acetone with a molar excess of phenol in the presence of a first solid acid catalyst promoted with a thiol under conditions effective to produce a first effluent stream comprising bisphenol isomers, unreacted phenol, trisphenols, organic sulfides and water;

(b3) recovering bisphenol-A from the first effluent stream to leave a residual stream comprising a mixture of bisphenol isomers depleted in bisphenol-A, unreacted phenol, trisphenols, organic sulfides and water;

(c3) dividing the residual stream into a first portion and a second portion; (d3) contacting the first portion of the residual stream with a second catalyst under conditions effective to isomerize bisphenol isomers to bisphenol-A and to produce a second effluent stream;

(e3) recycling at least part of the second effluent stream to step (a3) or step (b3);

(f3) contacting the second portion of the residual stream with a third catalyst under conditions sufficient to allow acid-catalyzed hydrolysis of organic sulfides in the second portion of the residual stream to the corresponding thiols and produce a third effluent stream;

(g3) distilling the third effluent stream to recover distillate products comprising phenols and thiols and produce a bottoms product comprising bisphenol isomers and trisphenols, and having a lower content of organic sulfides than the residual stream and (h3) supplying the distillate products recovered in step (g3) to step (a3).

DETAILED DESCRIPTION

The present invention relates to the production of bisphenols by the acid catalyzed condensation of carbonyl compounds with phenols in the presence of sulfur-containing promoters. In particular, the present invention provides a simple process for treating the residual streams remaining after recovery of the desired bisphenol product so as to convert sulfide by-products of the condensation reaction to thiols which can then be recycled back to the condensation reaction.

The present process is applicable to the acid-catalyzed condensation reaction between any carbonyl compound reactant and any phenolic compound reactant to produce a bisphenol product. Examples of suitable carbonyl compounds are those compounds represented by the following formula:

wherein R represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated; n is greater than 0, preferably from 1 to 3, more preferably from 1-2, and most preferably is 1; and when n is greater than 1, X represents a bond, or a multivalent linking group having from 1 to 14 carbon atoms, preferably from 1 to 6 carbon atoms, more preferably from 1 to 4 carbon atoms; and when n is 1, X represents hydrogen or an aliphatic, cycloaliphatic, aromatic, or heterocyclic radical, including hydrocarbon radicals such as alkyl, cycloalkyl, aryl, aralkyl, alkaryl, whether saturated or unsaturated, provided that X and R are not both hydrogen.

Suitable carbonyl compounds for use herein include aldehydes and ketones. These compounds generally contain from three to fourteen carbon atoms, and are preferably aliphatic ketones. Examples of suitable carbonyl compounds include ketones such as acetone, methyl ethyl ketone, diethyl ketone, dibutyl ketone, isobutyl methyl ketone, acetophenone, methyl and amyl ketone, cyclohexanone, 3,3,5-trimethylcyclohexanone, cyclopentanone, 1,3-dichloroacetone and the like. The most preferred is acetone.

The carbonyl compounds are reacted with phenolic compounds. Phenolic compounds suitable for use herein include phenol and the homologues and substitution products of phenol containing at least one replaceable hydrogen atom directly bonded to the aromatic phenol nucleus. Such groups substituting for the hydrogen atom and directly bonded to the aromatic nucleus include the halogen radicals such as chloride and bromide, and the hydrocarbon radicals such as alkyl, cycloalkyl, aryl, alkaryl and aralkyl groups. Suitable phenolic compounds include phenol, the cresols, the xylenols, carvacrol, cumenol, 2-methyl-6-ethyl phenol, 2,4-dimethyl-3-ethylphenol, o-chlorophenol, m-chlorophenol, o-t-butylphenol, 2,5-xylenol, 2,5-di-t-butylphenol, o-phenylphenol, 4-ethylphenol, 2-ethyl-4-methylphenol, 2,3,6-trimethylphenol, 2-methyl-4-tertbutylphenol, 2-tert-butyl-4methylphenol, 2,3,5,6-tetramethylphenols, 2,6-dimethylphenol, 2,6-ditertbutylphenol, 3,5-dimethylphenol, 2-methyl-3,5-diethylphenol, o-phenylphenol, p-phenylphenol, naphthols, phenanthrol, and the like. Most preferred are compositions comprising phenol. Mixtures of any of the above may be used.

The bisphenol compounds obtained by the condensation reaction of a phenolic compound and a carbonyl compound in the present process are compounds wherein the nuclei of at least two phenolic radicals are directly attached by carbon to carbon linkages to the same carbon atom in an alkyl group. An illustrative non-limiting example of a bisphenol compound is represented by the formula:

wherein $R_1$ and $R_2$ each independently represent a monovalent organic radical. Examples of such radicals include hydrocarbon radicals such as aliphatic, cycloaliphatic, aromatic, or heterocyclic radical, more specifically hydrocarbon radicals such as alkyl, cycloalkyl, aryl, aralkyl, alkaryl, whether saturated or unsaturated. Preferably, $R_1$ and $R_2$ each independently represent an alkyl radical having from 1 to 2 carbon atoms. Most preferably, the bisphenol compound comprises 2,2-bis (4-hydroxyphenyl) propane, i.e. bisphenol-A (BPA).

The reaction conditions used to effect the condensation reaction described above will vary depending on the type of phenolic compound, solvent, carbonyl compound, and condensation catalyst selected. Generally, the phenolic compounds and the carbonyl compounds are reacted in a reaction vessel, whether in the batch or continuous mode, at a temperature ranging from about 20° C. to about 130° C., preferably from about 50° C. to about 90° C.

The pressure conditions are not particularly limited and the reaction may proceed at atmospheric, sub atmospheric or super atmospheric pressure. However, it is preferred to run the reaction either without any externally induced pressure, or at sufficient pressure to force the reaction mixture across a catalyst bed or to force the reaction mixture upstream in a vertical reactor, or to maintain the contents of the reaction vessel in a liquid state if the reaction is run at a temperature above the boiling point of any ingredient. The pressure and temperature should be set under conditions to retain the reactants in the liquid phase in the reaction zone. The temperature may exceed 130° C., but should not be so high as to degrade any of the ingredients in the reaction vessel, nor should it be so high as to degrade the reaction product or promote the synthesis of a substantial amount of unwanted by-products.

The reactants are introduced into the reaction zone under conditions to assure a molar excess of the phenolic compound over the carbonyl compound. For example, the molar ratio of the phenolic compound to the carbonyl compound is preferably at least about 2:1, more preferably at least about 4:1, and up to about 25:1.

The condensation reaction is conducted in the presence of an acidic heterogeneous catalyst promoted by at least one organic sulfur-containing compound. Suitable catalysts include molecular sieves, salts of heteropolyacids partially neutralized and insolubilized, and acidic cation exchange resins. Preferred condensation catalysts are cation exchange resins and especially those having a cation exchange capacity of at least about 0.5 and, more preferably, greater than about 4.0 meq/g dry weight. Particularly preferred are sulfonated cation exchange resins, such as sulfonated styrene-divinylbenzene copolymers, sulfonated cross-linked styrene polymers, phenol-formaldehyde-sulfonic acid resins, benzene-formaldehyde-sulfonic acid resins, perfluorinated sulfonic acid resins and the like. These include resins sold under such trade names as Amberlites or Amberlysts (Rohm and Haas Co.), DOWEX (Dow Chemical Co.), Permutit QH (Permutit Co.), Chempro (Chemical Process Co.), catalysts from Purolite, Lewatit® (LANXESS Deutschland GmbH), NAFION® (DuPont) and the like. Strong acid sulfonated styrene-divinylbenzene copolymer resins are preferred. Suitable cation exchange resins are made from sulfonated polymerized styrene monomer which has been cross linked with from about 1% to about 8% divinylbenzene (resin). Specific examples of suitable sulfonated resins are Amberlyst® 131, Lewatit® K-1221, Purolite® CT-122, Purolite® CT-124, Diaion™ SK104H, Tulsion® 38, and Dowex® 50WX4.

The condensation catalyst system also includes at least one organic sulfur-containing promoter, which generally contains at least one thiol, S—H, group. Such thiol promoters can be either ionically or covalently bonded to the heterogeneous acid catalyst or unbound to the heterogeneous acid catalyst and added separately to the condensation reaction. Non-limiting examples of bound promoters include mercaptoalkylpyridines, mercaptoalkylamines, thiazolidines and aminothiols. Non-limiting examples of unbound promoters include alkyl mercaptans, such as methyl mercaptan (MeSH) and ethyl mercaptan, mercaptocarboxylic acids, such as mercaptopropionic acid, and mercaptosulfonic acids.

The amount of organic sulfur-containing promoter employed in the catalyst system depends on the particular acidic heterogeneous catalyst employed and the condensation process to be catalyzed. In general, however, the organic sulfur-containing promoter is employed in an amount from 2 to 30 mol %, such as 5 to 20 mol %, based on the acid group (sulfonic group) in the acid ion exchanger.

Where the unbound thiol promoter is methyl mercaptan, and the carbonyl compound is acetone, 2,2-bis(methylthio) propane (BMTP) is formed in the presence of an acidic catalyst. In the presence of a hydrolyzing agent, BMTP dissociates in the reaction zone into methyl mercaptan and acetone as acetone is condensed with phenol to form BPA. A convenient hydrolyzing agent is water, which may be introduced into any of the feed charges, directly into the reaction zone, or may be produced in situ by the condensation reaction between the carbonyl compound and the phenolic compound. A molar ratio of water to BMTP catalyst promoter ranging from about 1:1 to about 5:1 is sufficient to adequately hydrolyze the BMTP catalyst promoter. This quantity of water is produced in situ under typical reaction conditions. Thus, additional water does not need to be introduced into the reaction zone, although water may optionally be added if desired.

Any suitable reactor may be used as the reaction zone. The reaction can occur in a single reactor, or in a plurality of reactors connected in series or in parallel. The reactor can be a back mixed or plug flow reactor, and the reaction can be conducted in a continuous or batch mode, and the reactor can be oriented to produce an up-flow or down-flow stream. In the case of the fixed bed flow system, the liquid space velocity of the mixture of the raw materials supplied to the reactor is usually 0.2 to 50 $hr^{-1}$. In the case of the suspended bed batch system, the amount of the strongly acid ion exchange resin used, although variable depending on the reaction temperature and pressure, is usually 20 to 100% by weight based on the mixture of the raw materials. The reaction time is usually 0.5 to 5 hours.

The main products of the condensation reaction are the desired bisphenol isomer, normally bisphenol-A, and water together with various by-products, including other bisphenol isomers, such as 2-(4-hydroxyphenyl)-2-(2-hydroxyphenyl) propane or o,p-BPA, trisphenols and other impurities, such as chromans and indanes, as well as unconverted phenol and in some cases unconverted carbonyl compound. In addition, the condensation reaction effluent also contains organic sulfides formed from the condensation of the thiol promoter with carbonyl, carbonyl derivatives, and unsaturated intermediates. One example is 2,2-bis(methylthio)propane (BMTP). Another example of such a sulfide is 4-methyl-4-methylthio-2-pentanone (MOM):

which can be produced by reaction of mesityl oxide with methyl mercaptan.

Any method known to those of skill in the art may be employed to recover the desired bisphenol product, typically bisphenol-A, from the condensation effluent. Generally, however, the crude effluent from the condensation reaction is fed to a first separator, such as a distillation column, where most of the water and any unreacted carbonyl compound can be removed as overhead while the desired bisphenol product, other bisphenol isomers, unreacted phenolic compound, and the heavy by-products (including organic sulfides) are recovered as a bottoms product. This bottoms product may be fed to a further separator. While crystallization is a common method of bisphenol-A separation, any known method of separating the desired bisphenol product from the bottoms product can be used depending upon the desired degree of purity of the bisphenol product.

The liquid phase mixture remaining after separation of the desired bisphenol product from the condensation effluent, whether by crystallization or any other method, is referred to herein as the "residual stream". Where the separation is by crystallization, the residual stream is conventionally referred to as the mother liquor. The composition of the residual stream can vary widely but, typically after distillation to remove and recycle added solvent and optionally to effect partial dewatering, the residual stream contains:

(a) up to 90 wt %, such as up to 80 wt %, for example up to 75 wt % of unreacted phenolic compound and in most cases at least 60 wt %, such as at least 65 wt %, for example at least 70 wt % of unreacted phenolic compound;

(b) up to 30 wt %, such as up to 25 wt %, for example up to 20 wt % of a mixture of bisphenol isomers depleted in the desired bisphenol isomer, generally bisphenol A, and in most cases at least 10 wt %, such as at least 15 wt %, for example at least 18 wt % of said mixture of bisphenol isomers;

(c) up to 20 wt %, such as up to 16 wt %, for example up to 12 wt % of trisphenolic and heavier aromatic compounds and in most cases at least 4 wt %, such as at least 6 wt %, for example at least 8 wt % of trisphenolic and heavier aromatic compounds;

(d) up to 0.6 wt % (6000 ppmwt), such as up to 0.4 wt %, such as up to 0.2 wt %, for example up to 0.1 wt % of organic sulfides and in most cases at least 0.01 wt %, such as at least 0.04 wt %, for example at least 0.06 wt % of organic sulfides; and (e) up to 1.0 wt %, such as up to 0.8 wt %, for example up to 0.6 wt % of water and in most cases at least 0.2 wt %, such as at least 0.3 wt %, for example at least 0.4 wt % of water.

For process economy, the residual stream undergoes various treatments to recover and recycle the unreacted phenolic compound and the bisphenol isomers. In addition, part of the residual stream is generally purged to avoid build-up of heavy aromatic compounds in the recycle loops of the process. The present invention provides a process for converting at least part of the organic sulfides present in the residual stream to thiols before any of the residual stream is purged so that the loss of thiol promoter through purging is minimized and disposal problems for the purge stream are reduced.

In particular, the presently disclosed process includes contacting at least a portion of the residual stream or a reaction product thereof with an acidic hydrolysis catalyst under conditions sufficient to allow acid-catalyzed hydrolysis of organic sulfides in the residual stream to the corresponding thiol and a carbonyl compound. The liberated carbonyl can then react with phenol in the residual stream to form a bisphenol isomer and water. Consumption of the carbonyl and production of water favors further conversion of the sulfides to thiols and carbonyls. A representative example of the hydrolysis reaction is the hydrolysis of 4-methyl-4-methylthio-2-pentanone which, as discussed above, can be produced in the methyl mercaptan-promoted manufacture of bisphenol-A and which can be hydrolyzed in the presence of an acid catalyst according to the following reaction:

Mesityl oxide is in equilibrium with acetone. Moreover, both carbonyls can undergo condensation with phenol in the presence of the acidic hydrolysis catalyst to form bisphenols and water.

Any known hydrolysis catalyst can be used to convert the organic sulfides in the residual stream to the corresponding thiols, although preferred catalysts include acidic ion exchange resins, especially sulfonated acidic ion exchange resins. In one embodiment, the hydrolysis catalyst comprises an acidic, sulfonated microreticular polystyrene ion exchange resin with 2%-6% divinylbenzene crosslinking. Suitable conditions for the hydrolysis reaction include a temperature from 60 to 110° C., such as 75 to 95° C., and a weight hourly space velocity WHSV of 1-10 $hr^{-1}$. The molar ratio of water to hydrolyzable organic sulfide in the feed stream to the hydrolysis reaction is not critical but typically is at least 2:1, such as at least 4:1 or greater, for example at least 20:1. Upper limits on the molar ratio of water to hydrolyzable organic sulfide are largely driven by practical concerns and can be up to 100:1 or more, such as up to 80:1. Any known reactor configuration can be used for the hydrolysis reaction but in one preferred embodiment the reactor operates liquid full, with downflow of the feed through the ion exchange resin catalyst bed.

The effluent from the hydrolysis reaction is fed to a distillation column where the thiols, being more volatile than the corresponding sulfides, are recovered in the overhead stream with water and the unreacted phenolic compound. The bottoms product comprises bisphenol isomers, trisphenols and heavier aromatic products and has a lower content of organic sulfides than the residual stream. Typically, the bottoms product contains less than 100 ppm by weight, such as less than 10 ppm by weight, of organic sulfides. All or at least a part of the overhead products can then be recycled, generally without further separation, to the bisphenol manufacturing process, particularly the condensation reactor, while at least part of the bottoms product can be used in a downstream process, undergo further treatment to recover more phenol, acetone and/or isopropenyl phenol, and/or be purged for disposal. In the case of bisphenol-A production, suitable operating conditions for the distillation column include a temperature of 160° C. to 220° C. and a pressure of 75 mmHga to 200 mmHga.

In one implementation of the present process, the residual stream is divided into first and second portions without any initial treatment of the residual stream (except for solvent removal and partial dewatering). The first portion of the residual stream is then supplied to an isomerization reaction zone, as described below, while the second portion is supplied to the hydrolysis reactor described above. The relative amounts of the first and second portions of the residual stream are not critical but in some embodiments the second portion comprises at least 1 wt %, such as at least 3 wt %, of the total residual stream, but generally not more than 6 wt %, such as not more than 5 wt % of the total residual stream.

The isomerization reaction zone employed in said one implementation of the present process can include any known acid catalyst effective under the conditions in the isomerization reaction zone to isomerize a non-equilibrium mixture of bisphenol isomers, especially a mixture depleted in the desired bisphenol isomer. A suitable isomerization catalyst comprises an acidic ion exchange resin, especially a sulfonated acidic ion exchange resin. Suitable isomerization conditions include a temperature from 60 to 100° C., such as 75 to 85° C., and a weight hourly space velocity WHSV of 1-10 hr$^{-1}$. The effluent from the isomerization reaction zone has a higher content of the desired bisphenol isomer, such as p,p-BPA, than the residual stream and can be recycled to the bisphenol manufacturing process, such as to the condensation reactor or the crystallizer, for selective recovery of the desired bisphenol isomer.

In a further implementation of the present process, the entire residual stream is supplied to a combined isomerization/hydrolysis reaction zone containing one or more catalysts effective under the conditions in the reaction zone to isomerize a non-equilibrium mixture of bisphenol isomers, especially a mixture depleted in the desired bisphenol isomer, and to hydrolyze organic sulfides to the corresponding thiols. Suitable catalysts for effecting the combined isomerization/hydrolysis reaction comprise acidic ion exchange resins, especially sulfonated acidic ion exchange resins. Suitable isomerization/hydrolysis conditions include a temperature from 60 to 110° C., such as 80 to 90° C., and a weight hourly space velocity WHSV of 1-10 hr$^{-1}$.

The effluent from the isomerization/hydrolysis reaction zone has a higher content of the desired bisphenol isomer, such as p,p-BPA, than the residual stream and a lower content of organic sulfides than the residual stream. The effluent is then divided into a first and second portions, with the first portion being recycled to the bisphenol manufacturing process, particularly the crystallizer for selective recovery of the desired bisphenol isomer, and the second portion being supplied to a distillation column. The relative amounts of the first and second portions of the isomerization/hydrolysis effluent are not critical but in some embodiments the second portion comprises at least 1 wt %, such as at least 3 wt %, of the total effluent, but generally not more than 6 wt %, such as not more than 5 wt % of the total effluent.

The distillation column which receives the second portion of the isomerization/hydrolysis effluent is operated under conditions such that the unreacted phenolic compound, water and thiols are recovered in the overhead stream, while the bottoms product comprises bisphenol isomers, trisphenols and heavier aromatic products and has a lower content of organic sulfides than the residual stream. All or at least a part of the overhead products can then be recycled, generally without further separation, to the bisphenol manufacturing process, particularly the condensation reactor, while at least part of the bottoms product can be used in a downstream process, undergo further treatment to recover more phenol, acetone and/or isopropenyl phenol, and/or be purged for disposal. In the case of bisphenol-A production, suitable operating conditions for the distillation column include a temperature of 160° C. to 220° C. and a pressure of 75 mmHga to 200 mmHga.

In a modification of the further implementation of the present process, the second portion of the isomerization/hydrolysis effluent is fed to a further hydrolysis reactor before being supplied to the distillation column. The further hydrolysis reactor converts additional organic sulfides present in the isomerization/hydrolysis effluent back into thiols for recovery in the overhead of the distillation column.

Figure 1:
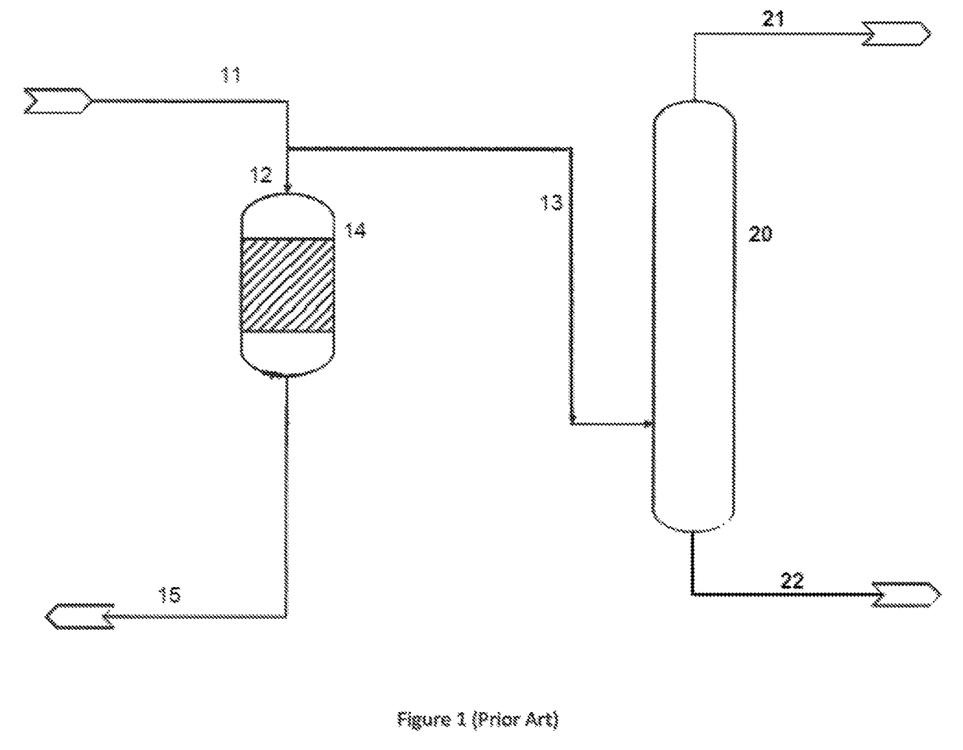
FIG. 1 illustrates a typical process for treating a residual stream from a bisphenol-A manufacturing process.

Referring to the drawings, in the current state of the art, as illustrated in FIG. 1, a crude product stream from a thiol-promoted bisphenol-A manufacturing process, that contains phenol, bisphenol-A and isomers thereof, trisphenols and other impurities, such as chromans and indanes, water, and sulfides formed from condensation of the thiol promoter with acetone, is purified, typically in a crystallizer (not shown), to recover the desired bisphenol-A. As shown in FIG. 1, the bisphenol-A-depleted residual stream (11) remaining after separation of solids from the crystallization effluent and distillation to recover any solvent employed in the crystallization step, is split into a first portion (12) and a second portion (13). The first portion (12) is then supplied to an isomerization reactor (14) where it is contacted with an acid isomerization catalyst to convert the bisphenol-A-depleted mixture of bisphenol isomers in the first portion (12) back towards equilibrium concentration. The resulting isomerized effluent stream (15) is then recycled to the condensation reactor or crystallizer for recovery of additional bisphenol-A.

The second portion (13) of the residual stream (11) is fed to a distillation column (20), which separates the second portion (13) into a distillate stream (21) containing phenol and water and a bottoms product (22) containing BPA isomers, trisphenols and other impurities, typically including from about 0.01 to about 0.60 wt % of organic sulfides.

Figure 2:
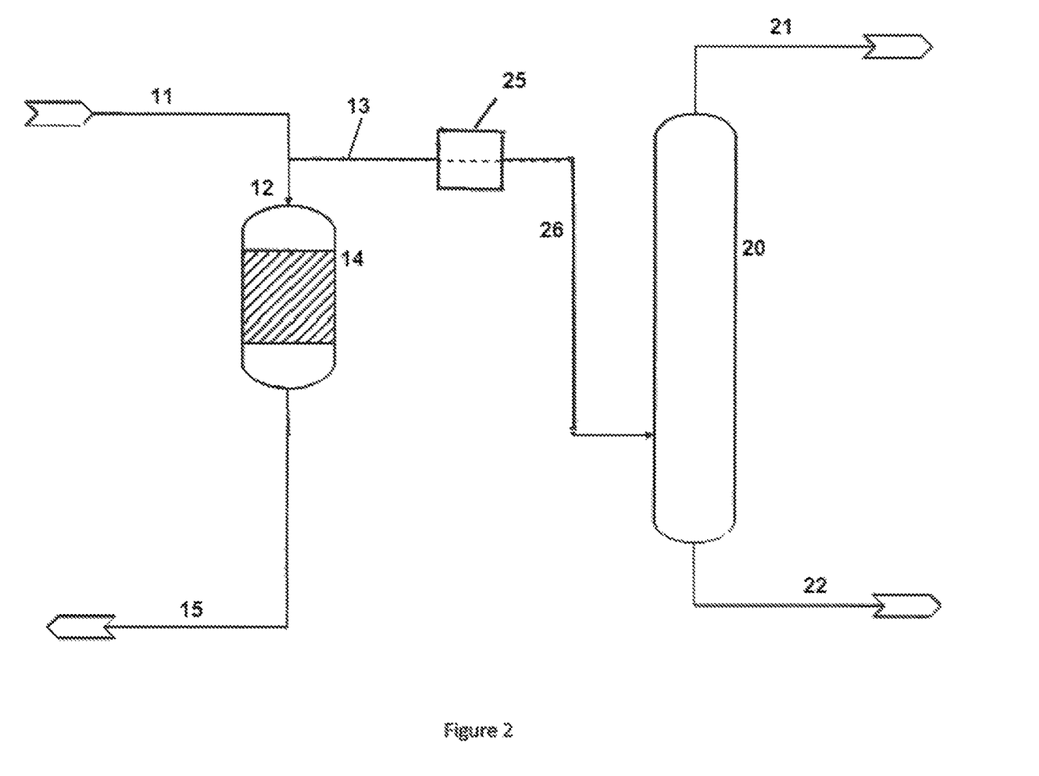
FIG. 2 illustrates a first embodiment of the process disclosed herein.
Figure 3:
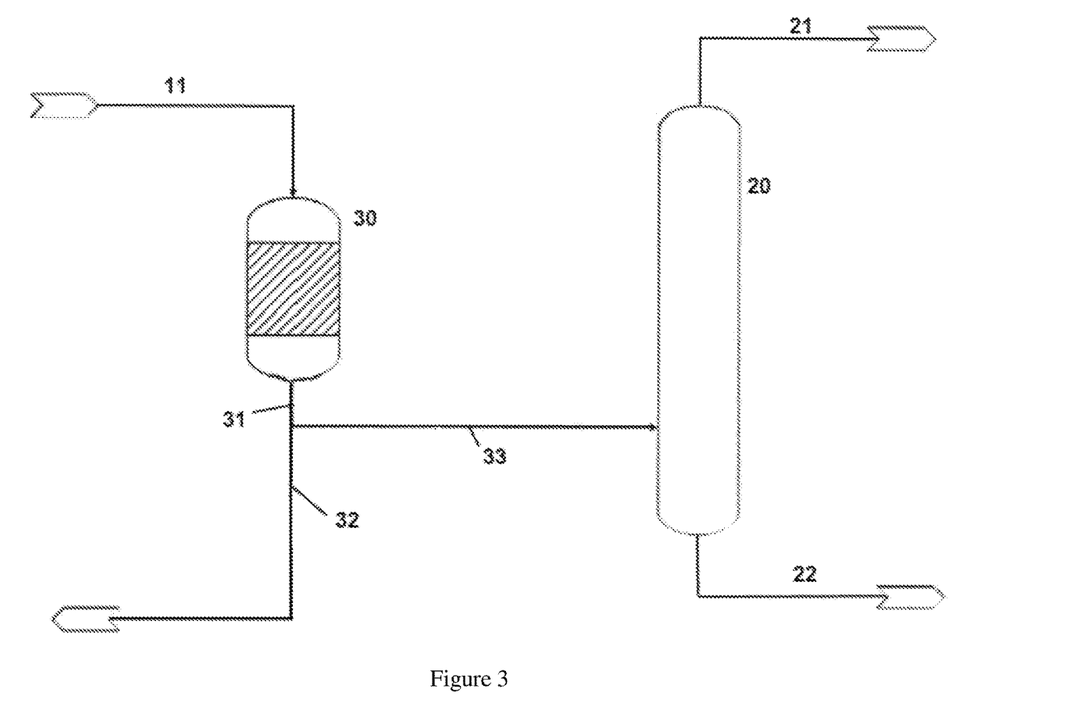
FIG. 3 illustrates a second embodiment of the process disclosed herein.
Figure 4:
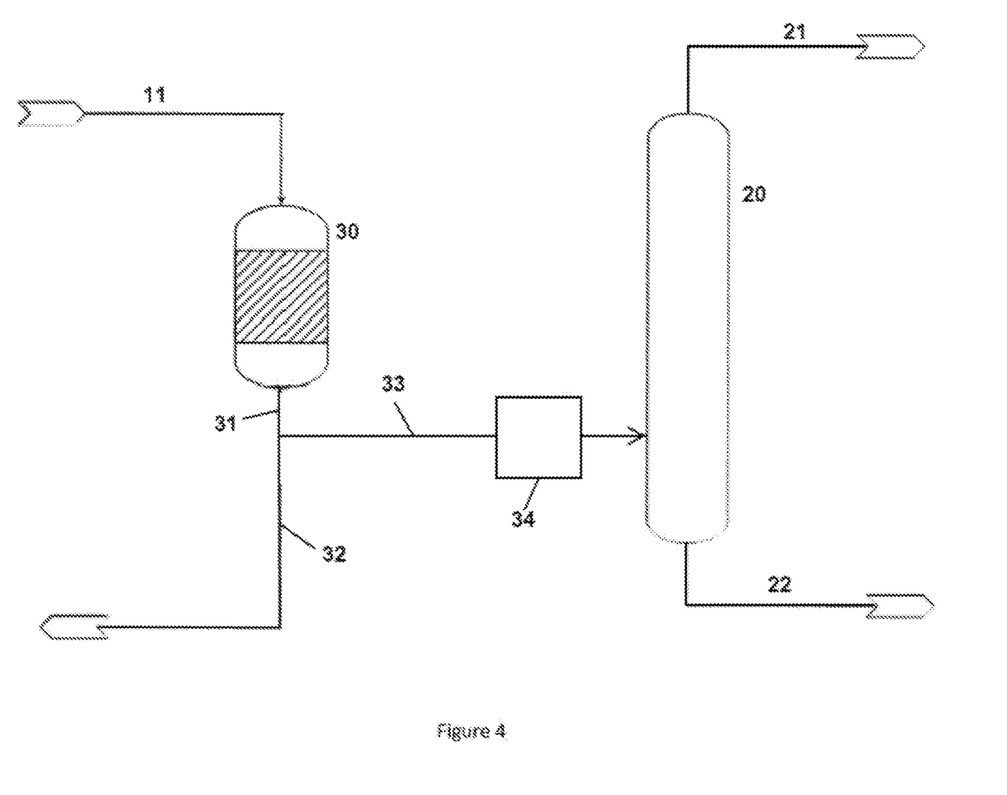
FIG. 4 illustrates a modification of the second embodiment of the process disclosed herein.

Various embodiments of the invention are shown in FIGS. 2 to 4, in which like reference numerals are used to identify like components to those shown in FIG. 1. In a first embodiment of the disclosed process, illustrated in FIG. 2, the residual stream (11) is again split into a first portion (12) and a second portion (13), with the first portion (12) being supplied to an isomerization reactor (14) for contact with an acid isomerization catalyst. However, in this first embodiment of the disclosed process, the second portion (13) of the residual stream is supplied to a hydrolysis reaction zone (25) where organic sulfides are converted back to carbonyl compounds and thiols. The effluent (26) from the hydrolysis reaction zone (25) is then supplied to the distillation column (20) for separation into a distillate stream (21) which now contains thiols in addition to phenol and water and a bottoms product (22) which contains BPA isomers, trisphenols and other impurities, but less organic sulfides than the residual stream (11).

A second embodiment of the disclosed process is illustrated in FIG. 3, in which the entire residual stream (11) is supplied to an isomerization/hydrolysis reactor (30) where it is contacted with one or more acid isomerization and hydrolysis catalysts to convert the bisphenol-A-depleted mixture of bisphenol isomers in the residual stream (11) back towards equilibrium concentration and to hydrolyze at least part of the organic sulfides to the corresponding thiols. The effluent (31) from the isomerization/hydrolysis reactor (30) is then divided into a first portion (32), which is recycled back to the bisphenol-A manufacturing process and a second portion (33), which is supplied to the distillation column (20).

In a modification of this second embodiment shown in FIG. 4, the second portion (33) of the isomerization/hydrolysis reactor effluent is passed through a further hydrolysis reactor (34) before being supplied to the distillation column (20). The reactor (34) contains an acid catalyst, such as an ion exchange resin, effective to convert at least part of any remaining organic sulfides to the associated thiol.

The invention will now be more particularly described with reference to the following non-limiting Examples.

Example 1

A batch reactor system was used comprising a 500-ml three-necked, jacketed, round bottom flask, a two-stage condenser to minimize the loss of volatile components, and an ethylene glycol circulating bath for temperature control of the reaction mixture. A thermocouple inserted into the reactor monitors the reaction temperature throughout the experiments. A magnetic stirring bar provides constant mixing of the reactor.

The reactor was initially loaded with 170 grams of phenol and 30 grams of p,p- BPA isomer. Next, a volume of Diaion™ SK104H 4% crosslinked S-DVB ion exchange resin (IER), equivalent to 5 grams on a dry basis, was washed at least 5 times with deionized water. The IER was subsequently air dried overnight in the vent hood. Next, the IER is dried further using 1000 ml of phenol over a period of 2.5 hours in a Soxhlet extractor, prior to being charged to the reactor. The mixture of phenol/p,p-BPA/IER (initially at room temperature) is heated to 80° C. by circulating glycol through the reactor jacket. This step was performed under a nitrogen blanket and with constant stirring of the reactor medium to allow the IER and reaction mixture to equilibrate. During this period the p,p-BPA isomerizes to form equilibrium mixture of o,p-BPA and BPX as well as form impurities typically in the recycle stream of a BPA production process. After approximately 14 to 18 hours, the water content of the conditioned reaction medium is determined by GC/TCD analysis or by KF Coulometer and adjusted with deionized water to 0.50% wt. At least 40 minutes after the last water adjustment, 0.16 g of MOM is added to the reactor to obtain approx. 800 ppmwt at the start of the reaction. To minimize loss of MOM, the nitrogen purge to the reactor is shut and the reactor vent tubing is pinched closed throughout the reaction period. The duration of the batch run was 4 hours, with the timing of the experiment beginning upon the addition of MOM. An initial sample is taken from the reactor before adding the MOM. The sampling of the reaction mixture was performed using a syringe injected through a septum. Reactor was sampled in 1-hour intervals after the addition of MOM. Each sample was labelled (0 to 4) and prepared according to internal standard protocols for HPLC analysis and sulfur speciation (GC/SCD). The MOM concentrations in ppmwt for each sample are shown in Table 1. The initial MOM concentration was calculated based on the added weights of phenol, BPA, water and MOM.

Examples 2 Through 6

For these examples the batch reaction described in Example 1 was repeated using the same conditions except that the measured water concentration of sample taken immediately before MOM addition (sample 0) was varied as shown in Table 1.

Examples 7 Through 10

For these examples the batch reaction described in Example 1 was repeated using the same conditions except that the reaction temperatures were increased to 95° C. for Example 7 and Example 8, and were decreased to 65° C. for Example 9 and Example 10.

Example 11

For Example 11 the batch reaction described in Example 1 was repeated using a volume of 4% crosslinked S-DVB ion exchange resin equivalent to 10 grams on a dry basis instead of 5 grams.

Examples 12 Through 15

For Examples 12 through 15 the batch reaction described in Example 1 was repeated using a volume of 2% cross-linked S-DVB ion exchange resin (Purolite® CT-122) equivalent to 5 dry grams instead of 4% cross-linked S-DVB ion exchange resin.

Example 16

For Example 16 the batch reaction described in Example 1 was repeated using 1.345 grams of MOM to obtain an initial concentration of approximately 6,300 ppmwt with a water concentration of 0.29% wt.

Figure 5:
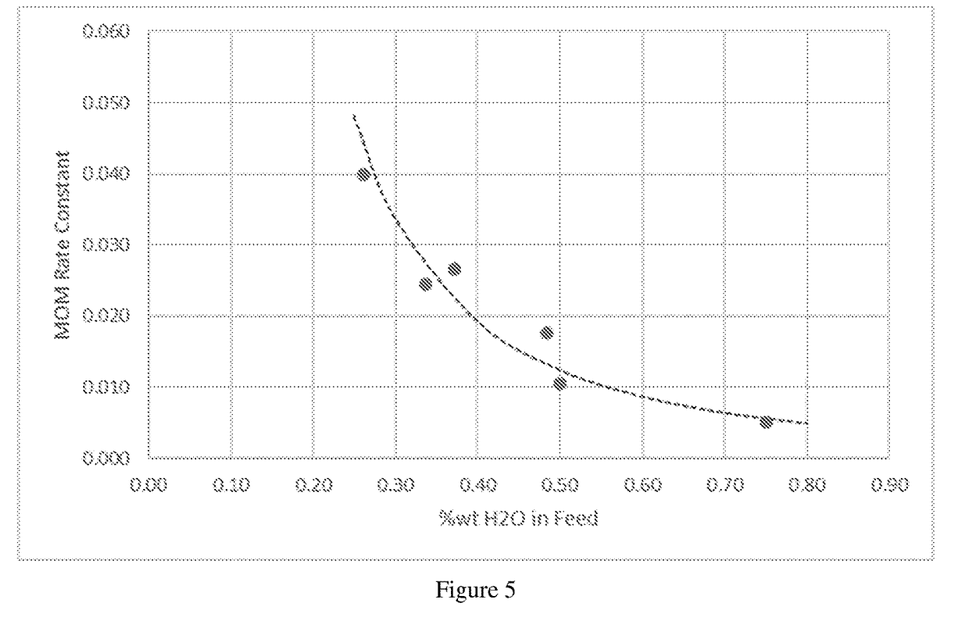
FIG. 5 shows the correlation in the first-order reaction rate constant for the decrease in 4-methyl-4-methylthio-2-pentanone (MOM) concentration as a function of the water concentration in the reaction feed for a batch reaction of about 750 ppmwt MOM in phenol in the presence of a sulfonated strong acid ion exchange resin.

The measured MOM concentrations from Examples 1 to 6 can be plotted versus reaction time to show that the hydrolysis reaction rate is essentially first-order with respect to MOM. An experimental reaction rate constant, $k_{exp}$, can then be calculated as shown in the last column of Table 1. The experimental reaction rate constants for Examples 1-6 are plotted as a function of the initial water concentration in FIG. 5 which shows the MOM reaction rate constant is inversely proportional to the square of the initial water concentration. FIG. 5 suggests that the effective acidity of the ion exchange resin has a strong influence on MOM reaction rate and that the hydrolysis reaction rate is not limited by the water concentration as long as it is present in stoichiometric excess. The correlation between the initial water concentration and the experimental reaction rate constants for Examples 1-6 was used to calculate an adjusted experimental reaction rate constant, $k_{0.5\ wt\ \%}$, at a nominal initial water concentration of 0.5% wt. The expected value of $k_{0.5w\ \%}$ based on Examples 1-6 is 0.0125. The adjusted experimental rate constants for Examples 1-16 are shown in Table 2. The value in the rightmost column is R, the ratio of the adjusted experimental rate constant, $k_{0.5\ wt\ \%}$, to the expected value of 0.0125 derived from the correlation in FIG. 5. Examples with R values greater than 1 had a higher reaction rate than the water adjusted rate correlation for the temperature, catalyst type, and catalyst loading rate used in Examples 1-6. Examples with R values less than 1 had a

TABLE 1

| Example | ° C. | gm cat | gm feed | % H2O | $[MOM]_0$ | $[MOM]_1$ | $[MOM]_2$ | $[MOM]_3$ | $[MOM]_4$ | $k_{exp}$ |
|---|---|---|---|---|---|---|---|---|---|---|
| 1 | 80 | 5 | 219.9 | 0.50% | 734 | 552 | 269 | 137 | 39 | 0.0106 |
| 2 | 80 | 5 | 212.9 | 0.48% | 766 | 393 | 79 | 39 | 9 | 0.0177 |
| 3 | 80 | 5 | 215.4 | 0.75% | 747 | 559 | 362 | 311 | 227 | 0.0051 |
| 4 | 80 | 5 | 212.1 | 0.37% | 763 | 127 | 23 | 8 | 0 | 0.0267 |
| 5 | 80 | 5 | 213.3 | 0.26% | 754 | 56 | 7 | 0 | 0 | 0.0399 |
| 6 | 80 | 5 | 213.6 | 0.34% | 763 | 208 | 42 | 12 | 2 | 0.0244 | lower reaction rate than the water adjusted rate correlation for the temperature, catalyst type, and catalyst loading rate used in Examples 1-6.

TABLE 2

| Example | % H2O | $k_{exp}$ | $k_{0.5\% \, w}$ | R |
|---|---|---|---|---|
| 1 | 0.50% | 0.0106 | 0.0106 | 0.85 |
| 2 | 0.48% | 0.0177 | 0.017 | 1.33 |
| 3 | 0.75% | 0.0051 | 0.0113 | 0.90 |
| 4 | 0.37% | 0.0267 | 0.0150 | 1.20 |
| 5 | 0.26% | 0.0399 | 0.0113 | 0.90 |
| 6 | 0.34% | 0.0244 | 0.0113 | 0.90 |
| 7 | 0.55% | 0.0385 | 0.047 | 3.76 |
| 8 | 0.41% | 0.0609 | 0.042 | 3.33 |
| 9 | 0.23% | 0.0230 | 0.005 | 0.41 |
| 10 | 0.49% | 0.0057 | 0.005 | 0.43 |
| 11 | 0.47% | 0.0312 | 0.028 | 2.26 |
| 12 | 0.47% | 0.0218 | 0.019 | 1.53 |
| 13 | 0.54% | 0.0154 | 0.018 | 1.46 |
| 14 | 0.44% | 0.0210 | 0.017 | 1.33 |
| 15 | 0.55% | 0.0196 | 0.024 | 1.90 |
| 16 | 0.29% | 0.0413 | 0.0143 | 1.14 |

Example 16 demonstrates effective hydrolysis of MOM for concentrations up to 6,300 ppmwt at a 3.72:1 molar ratio of water to hydrolyzable organic sulfides. Table 3 shows the MOM concentration as a function of time for Example 16. The concentration of methyl mercaptan (MeSH) increased to stoichiometrically equivalent concentration.

TABLE 3

| Reaction Time, min | 0 | 60 | 120 | 180 | 240 |
|---|---|---|---|---|---|
| [MOM], ppmwt | 6,327 | 124 | 6.5 | 0 | 0 |
| [MeSH], ppmwt | 0 | 2,674 | 1,942 | 2,360 | 2,092 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A method for producing bisphenol-A comprising:
   (a2) condensing acetone with a molar excess of phenol in one or more condensation reactors and in the presence of a first solid acid catalyst promoted with a thiol under conditions effective to produce a first effluent stream comprising bisphenol isomers, unreacted phenol, trisphenols, organic sulfides and water;
   (b2) recovering bisphenol-A from the first effluent stream to leave a residual stream comprising a mixture of bisphenol isomers depleted in bisphenol-A, unreacted phenol, trisphenols, organic sulfides and water;
   (c2) contacting at least part of the residual stream with a second catalyst in a second reactor separate from the condensation reactor(s) under conditions effective to isomerize bisphenol isomers to bisphenol-A and to hydrolyze organic sulfides to the corresponding thiols and produce a second effluent stream;
   (d2) dividing the second effluent stream into a recycle stream and a purge stream;
   (e2) supplying the recycle stream to step (a2) or step (b2);
   (f2) contacting the purge stream with a third catalyst in a third reactor separate from the condensation reactor(s) and the second reactor under conditions sufficient to allow acid-catalyzed hydrolysis of organic sulfides in the purge stream to the corresponding thiols and produce a third effluent stream; and
   (g2) distilling the third effluent purge stream to recover distillate products comprising phenol and thiols and produce a bottoms product comprising bisphenol isomers and trisphenols and having a lower content of organic sulfides than the purge stream.

2. The method of claim 1, which further comprises recycling at least part of the distillate products to the condensing step (a2).

3. The method of claim 1, in which the second catalyst comprises an acidic ion exchange resin.

4. The method of claim 1, in which the second catalyst comprises a sulfonated acidic ion exchange resin with 2%-6% crosslinking.

5. The method of claim 1, in which the thiol promoter and the recovered thiol are alkanethiols.

6. The method of claim 1, in which the contacting step (c2) is conducted at a temperature from about 60 to 110° C.

7. The method of claim 1, in which the third catalyst comprises an acidic ion exchange resin.

8. The method of claim 1, in which the third catalyst comprises a sulfonated acidic ion exchange resin with 2%-6% crosslinking.

9. The method of claim 1 in which the contacting with a third catalyst is conducted at a temperature from about 60 to 110° C.

10. The method of claim 1, in which the residual stream comprises hydrolyzable organic sulfides in an amount up to 6,000 ppmwt and water present in a sufficient amount that the molar ratio of water to hydrolyzable organic sulfides is at least 4:1.

11. The method of claim 1, in which the recovering step (b2) comprises crystallization and the residual stream comprises a mother liquor stream from the crystallization.

12. A method for producing bisphenol-A comprising:
   (a3) condensing acetone with a molar excess of phenol in one or more condensation reactors and in the presence of a first solid acid catalyst promoted with a thiol under conditions effective to produce a first effluent stream comprising bisphenol isomers, unreacted phenol, trisphenols, organic sulfides and water;
   (b3) recovering bisphenol-A from the first effluent stream to leave a residual stream comprising a mixture of bisphenol isomers depleted in bisphenol-A, unreacted phenol, trisphenols, organic sulfides and water;
   (c3) dividing the residual stream into a first portion and a second portion;
   (d3) contacting the first portion of the residual stream with a second catalyst under conditions effective to isomerize bisphenol isomers to bisphenol-A and to produce a second effluent stream;
   (e3) recycling at least part of the second effluent stream to the condensing step (a3) or recovering step (b3);
   (f3) contacting the second portion of the residual stream with a third catalyst in a further reactor separate from the condensation reactor(s) under conditions sufficient to allow acid-catalyzed hydrolysis of organic sulfides in the second portion of the residual stream to the corresponding thiols and produce a third effluent stream; and
   (g3) distilling the third effluent stream to recover distillate products comprising phenols and thiols and produce a bottoms product comprising bisphenol isomers and trisphenols, and having a lower content of organic sulfides than the residual stream.

13. The method of claim 12, which further comprises recycling at least part of the distillate products to the condensing step (a3).

14. The method of claim 12, in which the second catalyst comprises an acidic ion exchange resin.

15. The method of claim 12, in which the second catalyst comprises an acidic sulfonated ion exchange resin with 2%-6% crosslinking.

16. The method of claim 12, in which the thiol promoter and the recovered thiol are alkanethiols.

17. The method of claim 12, in which the contacting step (d3) is conducted at a temperature from about 60 to 100° C.

18. The method of claim 12, in which the third catalyst comprises an acidic ion exchange resin.

19. The method of claim 12, in which the third catalyst comprises an acidic sulfonated ion exchange resin with 2%-6% crosslinking.

20. The method of claim 12, in which the contacting step (f3) is conducted at a temperature from about 60 to 110° C.

21. The method of claim 12, in which the residual stream in step (b3) comprises hydrolyzable organic sulfides in an amount up to 6,000 ppmwt and water present in a sufficient amount that the molar ratio of water to hydrolyzable organic sulfides is at least 4:1.

22. The method of claim 12, in which the recovering step (b03) comprises crystallization and the residual stream comprises a mother liquor stream from the crystallization.

* * * * *